United States Patent [19]

Urdea et al.

[11] Patent Number: 5,258,506
[45] Date of Patent: Nov. 2, 1993

[54] PHOTOLABILE REAGENTS FOR INCORPORATION INTO OLIGONUCLEOTIDE CHAINS

[75] Inventors: Michael S. Urdea, Alamo; Thomas Horn, Berkeley, both of Calif.

[73] Assignee: Chiron Corporation, Emeryville, Calif.

[21] Appl. No.: 398,711

[22] Filed: Aug. 25, 1989

Related U.S. Application Data

[63] Continuation-in-part of Ser. No. 251,152, Sep. 29, 1988, which is a continuation-in-part of Ser. No. 661,508, Oct. 16, 1984, Pat. No. 4,775,619.

[51] Int. Cl.$^5$ .............................................. C07H 21/02
[52] U.S. Cl. ...................................... 536/23.1; 435/6; 436/501; 935/77; 935/78; 536/25.32
[58] Field of Search ............... 435/6, 91; 935/77, 78; 436/518, 527, 532, 501; 536/27, 23.1, 25.32

[56] References Cited

U.S. PATENT DOCUMENTS 4,302,204 11/1981 Wahl et al. ............................. 435/6
4,775,619 10/1988 Urdea ..................................... 435/6
5,118,605 6/1992 Urdea ..................................... 435/6

OTHER PUBLICATIONS

Gough et al, Tetrahedron Letters, 22 (1981) pp. 4177–4180.
J. Herbert et al., Can. J. Chem. 52:187–189 (1974).
M. Rubenstein et al., Tet. Lett. 17:1445–1448 (1975).

Primary Examiner—Amelia B. Yarbrough
Attorney, Agent, or Firm—Dianne E. Reed; Kenneth M. Goldman; Robert P. Blackburn

[57] ABSTRACT

Novel photolabile photochemical reagents are disclosed. The reagents are useful in a variety of biochemical and chemical contexts, including nucleic hybridization assays and chemical phosphorylation of hydroxyl-containing compounds. The reagents are particularly useful for introducing cleavable sites into oligonucleotide or polynucleotide chains, i.e., sites which are cleavable upon photolysis. The reagents are also useful in both 5'- and 3'-phosphorylation of oligonucleotide or polynucleotide chains.

9 Claims, No Drawings

PHOTOLABILE REAGENTS FOR INCORPORATION INTO OLIGONUCLEOTIDE CHAINS

CROSS-REFERENCE TO RELATED APPLICATIONS

This application is a continuation-in-part of U.S. patent application Ser. No. 251,152, filed Sep. 29, 1988, which is a continuation-in-part of U.S. patent application Ser. No. 661,508, filed Oct. 16, 1984 and issued Oct. 4, 1988 as U.S. Pat. No. 4,775,619.

TECHNICAL FIELD

The invention relates generally to photolabile chemical reagents, and more particularly relates to a novel class of photolabile reagents useful in a variety of contexts. The invention also relates to methods of using the novel reagents in biochemical assays and in phosphorylation reactions.

BACKGROUND

Incorporation of selectably cleavable sites into oligonucleotide and polynucleotide chains has been described in parent application Ser. No. 251,152 and grandparent U.S. Pat. No. 4,775,619, the disclosures of which are incorporated by reference herein. Selectably cleavable sites are useful in a number of different types of hybridization assay formats. For example, in one type of assay in which hybridization gives rise to a solid-supported duplex of a labeled probe and sample DNA, a selectably cleavable site contained within the hybrid structure will enable ready separation of the label from the solid support. U.S. Pat. No. 4,775,619 is primarily directed to the use of restriction endonuclease-cleavable sites in such assays, while parent application Ser. No. 251,152 concerns chemically cleavable sites, e.g., disulfide linkages, 1,2-diols, and the like. These chemically cleavable sites can be introduced during oligonucleotide synthesis, and are cleavable with particular chemical reagents, e.g., with thiols, periodate, or the like.

The present invention is also directed to selectably cleavable sites. However, the present method involves introduction of sites which are cleavable by photolysis rather than by treatment with chemical or enzymatic reagents. The cleavable sites of the invention are created by incorporation of photolabile chemical moieties into oligonucleotide or polynucleotide chains. The novel photolabile moieties are useful in a number of different types of hybridization assay formats, including those described in the above-cited parent and grandparent applications hereto, as well as in the amplification nucleic acid hybridization assay described in co-pending, commonly assigned U.S. patent application Ser. No. 252,638, filed Sep. 30, 1988, also incorporated by reference herein. The polynucleotide reagents of the invention which are synthesized so as to contain sites cleavable by photolysis are in general more stable to a variety of chemical conditions than the cleavable sites of the above-cited applications.

Another use of the reagents of the invention is in chemical phosphorylation. In many different aspects of oligonucleotide chemistry, chemical phosphorylation of hydroxyl groups is necessary. For example, in oligonucleotides synthesis, after synthesis and deprotection, the free 5'-hydroxyl group of the oligonucleotide must be phosphorylated for use in most biological processes. Also, phosphorylation of the 3'-hydroxyl functionality is typically necessary to generate oligonucleotides in a form that can be purified, stored and/or commercialized. See Sonveaux, *Bioorqanic Chem.* 14:274-294 (1986).

5'-phosphorylation has conventionally been carried out with T4 polynucleotide kinase and ATP, a reaction that is not particularly reliable or efficient. Several methods for chemical 5'-phosphorylation are also known, including those described by Nadeaux et al., *Biochemistry* 23:6153-6159 (1984), van der Marel et al., *Tetrahedron Letters* 22:1463-1466 (1981), Himmelsbach and Pfleiderer, *Tetrahedron Letters* 23:4793-4796 (1982), Marugg et al., *Nucleic Acids Research* 12:8639-8651 (1984), and Kondo et al., *Nucleic Acids Research Symposium Series* 16:161-164 (1985). However, most of these methods involve the use of unstable reagents or require extensive modification of standard deprotection and purification procedures. Similar problems have been found with monofunctional and bifunctional 3'-phosphorylating reagents (see Sonveaux, supra, at 297).

Thus, in addition to utility in providing cleavable sites within oligonucleotide or polynucleotide chains, sites which do not require chemical or enzymatic cleavage, the compounds of the present invention are additionally useful as phosphorylating reagents which overcome the limitations of current phosphorylation procedures.

DESCRIPTION OF THE PRIOR ART

Background references which relate generally to methods for synthesizing oligonucleotides include those related to 5'-to-3' syntheses based on the use of β-cyanoethyl phosphate protecting groups, e.g., de Napoli et al., *Gazz Chim Ital* 114:65 (1984), Rosenthal et al., *Tetrahedron Letters* 24:1691 (1983), Belagaje and Brush, *Nucleic Acids Research* 10:6295 (1977), in references which describe solutino-phase 5'-to-3' syntheses include Hayatsu and Khorana, *J. American Chemical Society* 89:3880 (1957), Gait and Sheppard, *Nucleic Acids Research* 4:1135 (1977), Cramer and Koster, *Angew. Chem. Int. Ed. Engl.* 7:473 (1968), and Blackburn et al., *Journal of the Chemical Society*, Part C, 2438 (1967).

In addition to the above-cited art, Matteucci and Caruthers, *J. American Chemical Society* 103:3185-3191 (1981), describe the use of phosphochloridites in the preparation of oligonucleotides. Beaucage and Caruthers, *Tetrahedron Letters* 22:1859-1862 (1981), and U.S. Pat. No. 4,415,732 describe the use of phosphoramidites in the preparation of oligonucleotides. Smith, ABL 15-24 (December 1983), describes automated solid-phase oligodeoxyribonucleotide synthesis. See also the references cited therein, and Warner et al., DNA 3:401-411 (1984), whose disclosure is incorporated herein by reference.

Horn and Urdea, DNA 5.5:421-425 (1986), describe phosphorylation of solid-supported DNA fragments using bis(cyanoethoxy)-N,N-diisopropylaminophosphine.

References which relate to hybridization techniques in general include the following: Meinkoth and Wahl, *Anal. Biochemistry* 138:267-284 (1984), provide an excellent review of hybridization techniques. Leary et al., *Proc. Natl. Acad. Sci.* (USA) 80:4045-4049 (1983), describe the use of biotinylated DNA in conjunction with an avidin-enzyme conjugate for detection of specific oligonucleotide sequences. Ranki et al., Gene 21:77-85, describe what they refer to as a "sandwich" hybridization for detection of oligonucleotide sequences. Pfeuffer and Helmrich, *J. Biol. Chem.* 250:867-876 (1975), describe the coupling of guanosine-5'-O-(3-thiotriphosphate) to Sepharose 4B. Bauman et al., *J. Histochem. and Cytochem.* 29:227-237, describe the 3'-labeling of RNA with fluorescers. PCT Application WO/8302277 describes the addition to DNA fragments of modified ribonucleotides for labeling and methods for analyzing such DNA fragments. Renz and Kurz, *Nucl Acids. Res.* 12:3435-3444, describe the covalent linking of enzymes to oligonucleotides. Wallace, *DNA Recombinant Technology* (Woo, S., ed.) CRC Press, Boca Raton, Fla., provides a general background of the use of probes in diagnosis. Chou and Merigan, *N. Eng. J. of Med.* 308:921-925, describe the use of a radioisotope-labeled probe for the detection of CMV. Inman, *Methods in Enzymol.* 34B, 24:77-102 (1974), describes procedures for linking to polyacrylamides, while Parikh et al., *Methods in Enzymol.* 34B, 24:77-102 (1974), describe coupling reactions with agarose. Alwine et al., *Proc. Natl. Acad. Sci. (USA)* 74:5350-5354 (1977), describe a method of transferring oligonucleotides from gels to a solid support for hybridization. Chu et al., *Proc. Natl. Acad. Sci.* (USA) 11:6513-6529, describe a technique for derivatizing terminal nucleotides. Ho et al., *Biochemistry* 20 64-67 (1981), describe derivatizing terminal nucleotides through phosphate to form esters. Ashley and MacDonald, *Anal. Biochem* 140:95-103 (1984), report a method for preparing probes from a surface-bound template.

Hebert and Gravel, Can. J. Chem. 52:187-189 (1974), and Rubinstein et al., *Tetrahedron Lett.*, No. 17, pp. 1445-1448 (1975), describe the use of nitrophenyl-containing compounds as light-sensitive protecting groups.

DETAILED DESCRIPTION OF THE INVENTION

A. Definitions

By "selectably cleavable site" is meant a functionality or plurality of functionalities which can be selectively cleaved. The focus of the present invention, as noted hereinabove, is on sites which are specifically cleavable using photolysis.

By "oligonucleotide" is meant a nucleotide chain having from about 2 to about 100 component nucleotide monomers.

By "polynucleotide" is meant a nucleotide chain having generally 100 or more component nucleotide monomers. In general, for purposes of the present invention, the terms "oligonucleotide" and "polynucleotide" can be used interchangeably.

By "nucleic acid sample" is intended a sample suspected of containing a nucleic acid sequence of interest.

By "nucleic acid analyte" is intended DNA or RNA in said nucleic acid sample containing the sequence of interest.

By "phosphorylating reagents" as used herein are intended compounds which, upon a reaction or series of reactions with a hydroxyl-containing compound, will yield a phosphate triester.

B. Structure of the Novel Reagents

The reagents of the present invention are photolabile chemical compounds having the structure:

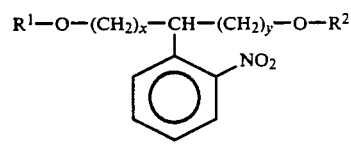

wherein $R^1$ is a base-stable, acid-sensitive blocking group, $R^2$ is a phosphorus derivative selected to enable addition of the reagent to the 5' position of a nucleoside or an oligonucleotide chain, and one of x and y is zero while the other is an integer in the range of 1 to 12 inclusive. Two basic types of structures fall within the above generic formula: (1) those wherein x is nonzero and y is zero (sometimes referred to herein as "NP1-type" reagents); and (2) those wherein x is zero and y is nonzero (sometimes referred to herein as "NP2-type" reagents). These two types of structures are, as may be readily inferred from the above generic formula, quite similar. They are each useful for introducing specific sites into oligonucleotide chains, which, because of the nitrophenyl moiety, are readily cleavable via photolysis. However, as will be discussed in more detail below, the two families of chemical reagents are distinguishable insofar as they are useful in slightly different contexts.

Turning now to the various substituents of the novel chemical reagents:

$R^1$ is, as noted above, a base-stable, acid-sensitive blocking group. Such blocking groups are well known in the art of oligonucleotide synthesis and include unsubstituted or substituted aryl or aralkyl groups, where the aryl is, e.g., phenyl, naphthyl, furanyl, biphenyl, or the like, and where the substituents are from 0 to 3, usually 0 to 2, and include any non-interfering stable groups, neutral or polar, electron-donating or withdrawing. Examples of such groups are dimethoxytrityl (DMT), monomethoxytrityl (MMT), trityl and pixyl. A particularly preferred moiety for use herein is DMT.

$R^2$ is a phosphorus derivative which is selected so as to facilitate condensation of the reagent with the 5'-hydroxyl group of a nucleoside or an oligonucleotide chain. Such groups include phosphoramidites, phosphotriesters, phosphodiesters, phosphites, H-phosphonates, phosphorothioates, and the like (see, e.g., EP Publication No. 0225807 by Urdea et al., "Solution Phase Nucleic Acid Sandwich Assay and Polynucleotide Probes Useful Therein", the disclosure of which is incorporated by reference herein). Particularly preferred groups useful as $R^2$ are phosphoramidites having the structure:

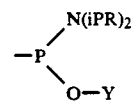

wherein Y is selected from the group consisting of methyl and β-cyanoethyl, and "iPr" represents isopropyl. Most preferably, Y is β-cyanoethyl.

As may be readily deduced from the above definitions, the $R^1$ and $R^2$ substituents are generally selected so as to allow incorporation of the photolabile reagent into a DNA fragment using standard phosphoramidite chemistry protocols. That is, during oligonucleotide synthesis, the $R^2$ substituent is selected so as to react with the 5'-hydroxyl group of a nucleoside or an oligonucleotide chain, while the $R^1$ moiety is selected so as to enable reaction with the 3'-hydroxyl of a nucleoside or an oligonucleotide chain.

With respect to the subscripts x and y, one of x and y is zero while the other is an integer in the range of 1 to 12 inclusive, more preferably in the range of 1 to 4 inclusive, and most preferably 1.

Exemplary reagents falling within the aforementioned general category are the following:

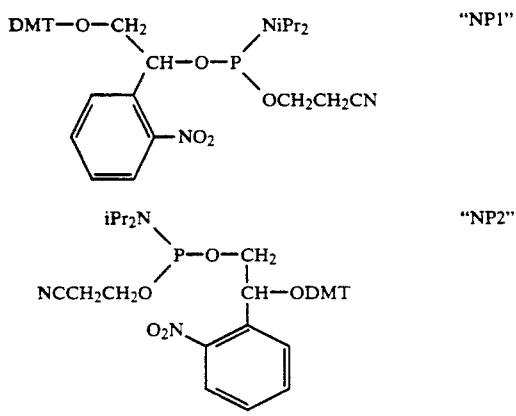

As indicated, these specific structures, [2-(2-nitrophenyl)-2-(O-dimethoxytrityloxy)ethoxy]-N,N-diisopropylamino-2-cyanoethoxyphosphine and [2-(2-nitrophenyl)-1-(O-dimethoxytrityloxy)ethoxy]-N,N-diisopropylamino-2-cyanoethoxyphosphine, are designated herein as compounds "NP1" and "NP2", respectively, and are the specific reagents synthesized in Examples 1 and 2 below.

C. Synthesis of the Novel Reagents

Reagents of NP1-type, that is, wherein x is nonzero and y is zero, are synthesized according to the reaction sequence outlined in Scheme 1. Reagents of the NP2-type are synthesized according to the set of reactions outlined in Scheme 2.

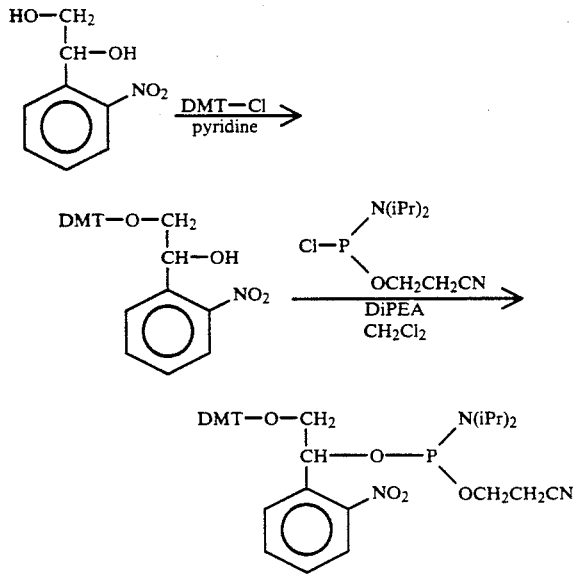

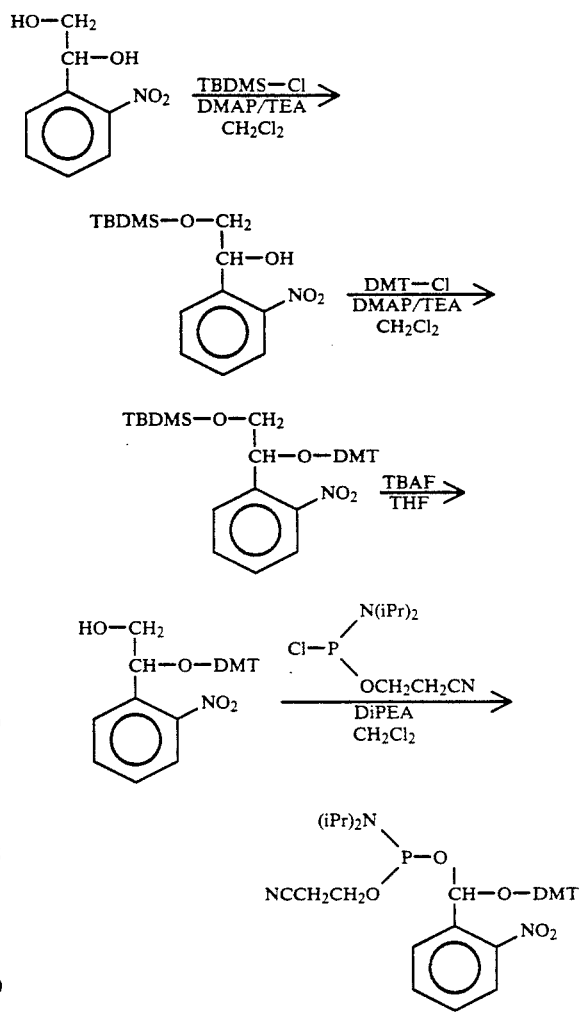

Abbreviations in Schemes 1 and 2: "DMT-Cl" = dimethoxytrityl chloride; "iPr" = isopropyl; "DiPEA"- = diisopropylethylamine; "TBDMS-Cl" = t-butyldimethylsilyl chloride; "DMAP" = dimethylaminopyridine; "TEA" = triethylamine; "TBAF" = tetrabutylammonium fluoride.

Synthesis of NP1-type reagents involves capping the terminal hydroxyl group of 2-(O-nitrophenyl)-1,2-ethanediol with the $R^1$ species, e.g., with DMT or the like, followed by reaction of the remaining hydroxyl group with a selected phosphorus derivative to give rise to the $R^2$ moiety As shown in Scheme 1, an exemplary reagent for this latter purpose is chloro-N,N-diisopropylamino-2-cyanoethoxyphosphine. Variations on this basic scheme may be readily deduced. For example, to provide different $R^1$ substituents, one would use monomethoxytrityl chloride, trityl chloride, pixyl chloride, or the like, as an alternative to dimethoxytrityl chloride. Similarly, to give rise to different $R^2$ substituents, alternative substituted phosphines would be employed in the second step of the reaction. To vary x, additional methylene groups are required in the initial starting material.

To synthesize reagents of the NP2-type, i.e., wherein x is zero and y is nonzero, a similar synthetic sequence is carried out, except that the order in which the $R^1$ and $R^2$ substituents are introduced is reversed. Thus, initially, the terminal hydroxyl group of the 2-(O-nitrophenyl)-1,2-ethanediol starting material is reacted with t-butyldimethylsilyl chloride ("TBDMS-Cl") to block that hydroxyl group during the next reaction step, in which the remaining free hydroxyl group, is reacted with a base-stable, acid-sensitive blocking group, e.g., dimethoxytrityl chloride ("DMT-Cl"), to provide the $R^1$ substituent. The terminal hydroxyl group is then deprotected, e.g., with tetrabutylammonium fluoride, and, as in Scheme 1, reacted with a suitable substituted phosphine derivative to give rise to the R2 moiety.

D. Use of the Novel Reagents to Create Selectably Cleavable Sites

The novel photolabile reagents of the invention are readily incorporated into an oligonucleotide or polynucleotide chain using standard phosphoramidite chemistry, well known in the art, and as described, for example, in a number of the references cited hereinabove. In general terms, incorporation of the novel reagent into a DNA fragment involves linkage to a 5'-hydroxyl group at $R^2$, and linkage to a 3'-hydroxyl group at $R^1$.

Thus, after incorporation of the photolabile reagent, the hybrid oligonucleotide chain will have the following structure:

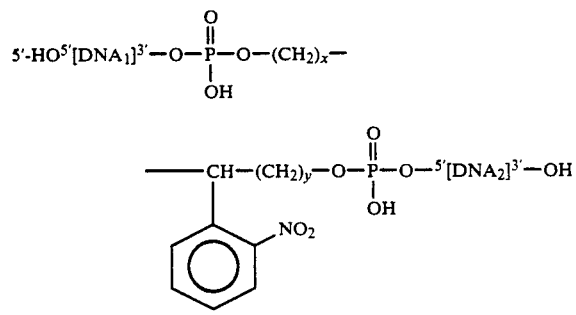

in which $DNA_1$ represents a first segment of DNA, $DNA_2$ represents a second segment of DNA, and x and y are as defined earlier. $DNA_1$ and $DNA_2$ may be either linear or branched. This polynucleotide reagent may be used in hybridization assays such as those described in parent application Ser. No. 251,152 and grandparent U.S. Pat. No. 4,775,619. These assays involve the use of linear polynucleotide reagents having selectable cleavage sites, i.e., wherein $DNA_1$ and $DNA_2$ are linear. The polynucleotide reagent containing the photolabile moiety of the invention may also be used in the amplification assay of U.S. patent application Ser. No. 252,638. As described in that application, cleavable "linker" molecules may be incorporated into amplification multimers at predetermined sites for the purpose of analyzing the structure of the multimer or as a means for releasing predetermined segments (such as the portion of the multimer that binds to the labeled oligonucleotide). In such an application $DNA_1$ and/or $DNA_2$ are branched polynucleotide segments. Subsequent to multimer synthesis and purification, the branched polynucleotide structure of the multimer can be cleaved specifically without additional degradation of the nucleotide structure. It is preferred, clearly, that the cleavable sites be introduced at or near the junctions of the multimer to enable quantitation of the individual multimer "branches".

Depending on whether the photolabile reagent incorporated into the oligonucleotide or polynucleotide is an NP1-type (i.e., wherein x is nonzero and y is zero) or an NP2-type (i.e., wherein x is zero and y is nonzero), two different types of fragments will result upon cleavage. That is, as illustrated in Scheme 3, cleavage of an oligonucleotide containing an NP1-type moiety will result in a first fragment having a terminal 5'-phosphate and a second fragment which at its 3'-terminus contains the residue nitrophenyl species. By contrast, as illustrated in Scheme 4, cleavage of a polynucleotide containing the NP2-type moiety will give rise to a first fragment containing the residual nitrophenyl group at its 5' terminus and a second fragment having a terminal 3'-phosphate.

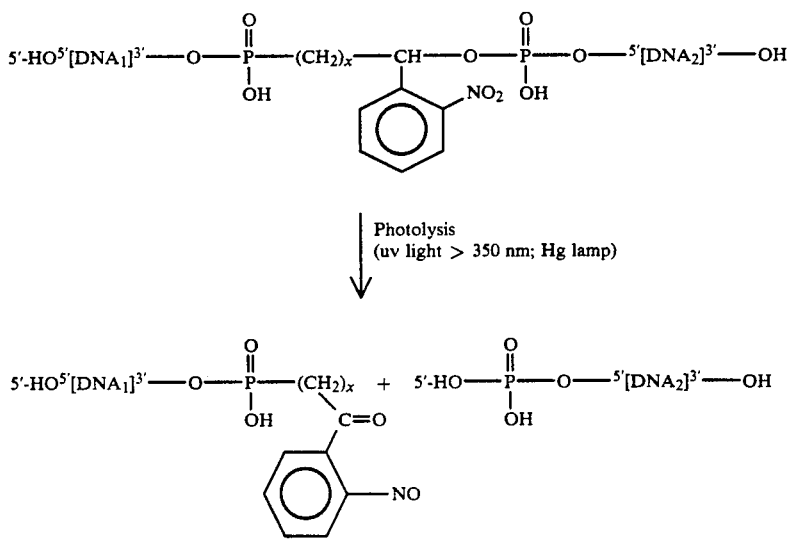

Scheme 3

Scheme 4

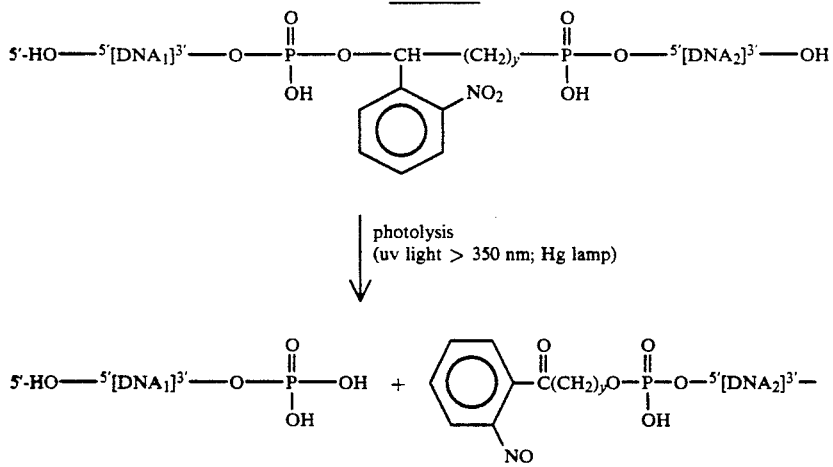

As cleavage is effected via photolysis, using uv light having a wavelength of at least about 350 nm, no enzymatic or chemical reagents are required. Thus, a cleaner procedure is provided, resulting in a product that is necessarily free of contamination with external cleavage reagents. In addition, the polynucleotide reagent itself is inherently more stable, cleavable as it is only by treatment with ultraviolet light of a suitable wavelength.

E. Phosphorylation Using the Novel Reagents

The reagents of the present invention, in addition to their utility in providing photolabile cleavage sites, are also useful as chemical phosphorylation reagents. Phosphorylation using these reagents involves condensation with a hydroxyl-containing compound, followed by photochemical cleavage and release of the nitrophenyl group. The novel reagents are quite versatile in this regard, as they may be used for either 5'- or 3'-phosphorylation of a nucleoside or an oligonucleotide chain.

For 5'-phosphorylation, an NP1-type reagent is required, i.e., a reagent wherein x is nonzero and y is zero. As illustrated in Scheme 3 above, cleavage of a polynucleotide reagent containing the NP1-type molecule results in a nucleoside or DNA fragment containing a 5'-phosphate group.

For 3'-phosphorylation, an NP2-type reagent is necessary, as illustrated in Scheme 4. Cleavage of a polynucleotide reagent containing the NP2-type molecule gives rise to cleavage fragments in which one of the fragments contains a 3'-phosphate group and the remaining fragment contains the nitrosophenyl residue.

It is to be understood that while the invention has been described in conjunction the preferred specific embodiments thereof, the foregoing description, as well as the examples which follow, are intended to illustrate and not limit the scope of the invention.

EXAMPLE 1

Synthesis of [2-(2-nitrophenyl)-2-(O-dimethoxytrityloxy)ethoxy]-N,N-diisopropylamino-2-cyanoethoxyphosphine ("NP1"): 2-(O-Nitrophenyl)-1,2-ethanediol (2.5 g, 13.6 mmole) was dried by coevaporation once with pyridine. The residue was dissolved in pyridine (50 ml) and 4,4'-dimethoxytrityl chloride (DMT-Cl) 13.6 mmole was added. The reaction mixture was stirred for 18 hours at 20° C. Most of the pyridine was then distilled off and the oily residue dissolved in 250 ml ethyl acetate. The organic phase was washed with 5% NaHCO$_3$ (2×250 ml), 80% saturated aqueous NaCl (1×250 ml), and dried over solid Na$_2$SO$_4$. After filtration, the solvent was removed in vacuo and the residue coevaporated with toluene (1×200 ml) and CH$_3$CN (1×200 ml). The product was purified on a column of silica gel (eluted with CH$_2$Cl$_2$—0.5% triethylamine) to give 6.5 g (13.6 mmole) pure product (100% yield).

The purified product of 1-O-DMT-2-(O-nitrophenyl)-1,2-ethane diol was converted to β-cyanoethyl phosphoramidite by reaction in CH$_2$Cl$_2$ (50 ml) with chloro-N,N-diisopropylamino-2-cyanoethoxy phosphine (15 mmole) in the presence of diisopropylethylamine (30 mmole) at 10° C. for 30 min. Ethyl acetate (200 ml) was then added and the combined organic phase washed with 80% saturated aqueous NaCl (2×250 ml) and dried over solid Na$_2$SO$_4$. After removal of the solvent in vacuo, the residue was coevaporated with toluene (100 ml) and CH$_3$CN (100 ml) to give 9.5 g of the 2-O-phosphoramidite of 1-O-dimethoxytrityl-2-(O-nitrophenyl)-1,2-ethanediol (100% yield).

EXAMPLE 2

Synthesis of [2-(2-nitrophenyl)-1-(O-dimethoxytrityloxy)ethoxy]-N,N-diisopropylamino-2-cyanoethoxy phosphine ("NP2"): 2-(O-Nitrophenyl)-1,2-ethanediol (2.5 g, 13.6 mmole) was dried by coevaporation with CH$_3$CN. The dried compound was then dissolved in CH$_2$Cl$_2$ (100 ml)-CH$_3$Cl (10 ml). N,N-Dimethylaminopyridine (100 mg) and triethylamine (3.6 ml, 26 mmole) were added, and, with stirring, solid t-butyldimethylsilyl chloride (TBDMS-Cl) (2.6 g, 15 mmole) was added. The stirring was continued for 18 hours at 20° C. Then more TBDMS-Cl (200 mg) was added. After one hour the reaction mixture was diluted with 400 ml ethyl acetate. The organic phase was washed with 5% NaHC03 (2x 250 ml) and 80% saturated aqueous NaCl (1×250 ml), and dried over solid Na$_2$SO$_4$. After removal of the solvents in vacuo, the residue was coevaporated with toluene (200 ml) and CH$_3$CN (200 ml) to give 2.5 g of crude 1-O-TBDMS-2-(O-nitropheyl)-1,2- ethanediol. The crude material was coevaporated with pyridine, and the residue was dissolved in pyridine (50 ml). DMT-Cl (30 mmole) was added and the reaction mixture stirred at 20° C. for 48 hours. After removal of the solvent in vacuo, the residue was dissolved in ethyl acetate (250 ml). The organic phase was washed with 5% NaHCO$_3$ (2×250 ml) and 80% saturated aqueous NaCl (1×250 ml), and dried over solid Na$_2$SO$_4$. After removal of the solvent in vacuo, the residue was coevaporated with toluene and CH$_3$CN. The residue was dissolved in THF (100 ml) and 10 ml of a 1M solution of tetrabutylammonium fluoride in THF was added. The removal of the 1-O-TBDMS group was complete in 30 min. The product was purified on a silica gel column to give pure 2-O-DMT-2-(O-nitrophenyl)-1,2-ethanediol (2.4 g, 4.5 mmole). This material was converted to the 2-cyanoethylphosphoramidite, as described above, in quantitative yield.

EXAMPLE 3

A test fragment 5'-T$_{15}$-3'-p-NP1-p-5'-T$_{20}$-3'-OH ("p"=phosphate) was assembled using standard phosphoramidite synthetic procedures. After complete deprotection, the purified DNA oligomer dissolved in H$_2$O was subjected to photolysis for 15 minutes (Hg lamp, λ>350 nm). PAGE analysis of the photolyzed sample showed that the treatment had resulted in complete cleavage of the test fragment into new fragments that migrated as would be expected for segments T$_{20}$ and T$_{15}$.

We claim:

1. A polynucleotide reagent having the structure

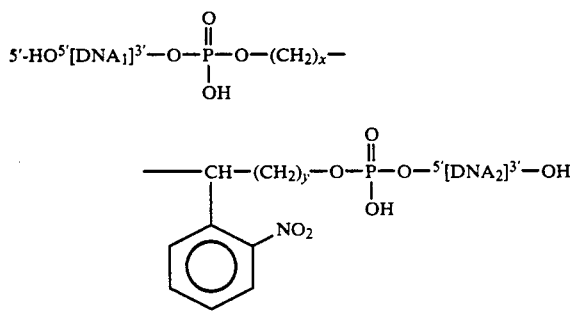

wherein
DNA$_1$ is a first segment of DNA;
DNA$_2$ is a second segment of DNA; and
one of x and y is zero while the other is an integer in the range of 1 to 12 inclusive.

2. The polynucleotide reagent of claim 1, wherein x is zero.

3. The polynucleotide reagent of claim 2, wherein y is an integer in the range of 1 to 4 inclusive.

4. The polynucleotide reagent of claim 3, wherein y is one.

5. The polynucleotide reagent of claim 1, wherein y is zero.

6. The polynucleotide reagent of claim 5, wherein x is an integer in the range of 1 to 4 inclusive.

7. The polynucleotide reagent of claim 6, wherein x is one.

8. A method for detecting the presence of an oligonucleotide sequence of interest in a nucleic acid analyte present in a nucleic acid sample, said method. comprising:
combining under hybridizing conditions said nucleic acid sample with the polynucleotide reagent of claim 1, wherein one of said sample or said reagent is bound to a support and hybridization of said analyte and said polynucleotide reagent results in a label being bound to said support through the cleavage site

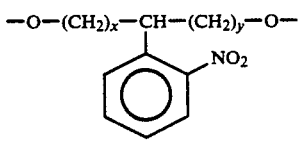

substantially freeing said support of label bound to said support other than through said selectable cleavage site;
cleaving said cleavage site via photolysis using light having a wavelength of at least about 350 nm; and detecting label free of said support.

9. A method for detecting the presence of an oligonucleotide sequence of interest in a nucleic acid analyte present in a nucleic acid sample, said method comprising:
combining under hybridizing conditions in an aqueous medium, said nucleic acid sample with the polynucleotide reagent of claim 1, where one of said sample or a component of said reagent is bound to a support and hybridization of said analyte and said polynucleotide reagent results in a label being bound to said support through the cleavage site

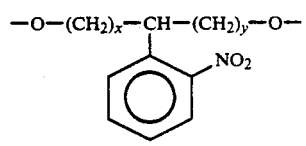

separating said support having bound polynucleotide reagent and nucleic acid analyte from said aqueous medium;
washing said support with a medium of different hybridizing stringency from said aqueous medium to remove label bound to said support other than through said cleavage site;
cleaving said cleavage site via photolysis using light having a wavelength of at least about 350 nm; and detecting label free of said support.

* * * * *